United States Patent
Abrutyn et al.

[11] Patent Number: 5,225,188
[45] Date of Patent: Jul. 6, 1993

[54] UNDERARM FORMULATIONS CONTAINING ALKYLMETHYLSILOXANES

[75] Inventors: Eric S. Abrutyn; Bradley C. Bahr; Gary E. Legrow; William J. Schulz, Jr., all of Midland, Mich.

[73] Assignee: Dow Corning Corporation, Midland, Mich.

[21] Appl. No.: 813,549

[22] Filed: Dec. 26, 1991

[51] Int. Cl.$^5$ .............. A61K 7/32; A61K 7/34; A61K 7/36; A61K 7/38
[52] U.S. Cl. .............. 424/66; 424/DIG. 5; 424/47; 424/65; 424/67; 424/68
[58] Field of Search .............. 424/47, 65, 68, 66

[56] References Cited

U.S. PATENT DOCUMENTS

| | | | |
|---|---|---|---|
| 4,073,880 | 2/1978 | Pader et al. | 424/66 |
| 4,083,956 | 4/1978 | Shelton | 424/66 |
| 4,152,416 | 5/1979 | Spitzer et al. | 424/46 |
| 4,174,386 | 11/1979 | Spitzer et al. | 424/47 |
| 4,275,222 | 6/1981 | Scala, Jr. | 560/103 |
| 4,574,082 | 3/1986 | Tietjen et al. | 424/63 |
| 5,002,762 | 3/1991 | Bolich | 424/70 |

*Primary Examiner*—Dale R. Ore
*Attorney, Agent, or Firm*—Roger E. Gobrogge

[57] ABSTRACT

This invention relates to an underarm formulation containing volatile and/or non-volatile alkylmethylsiloxanes. Incorporation of such agents results in formulations which have beneficial effects such as decreased whitening, less crumbling, better compatibility, controlled vapor pressure and better aesthetics. In addition, use of these materials often results in processing advantages over the prior art.

15 Claims, No Drawings

UNDERARM FORMULATIONS CONTAINING ALKYLMETHYLSILOXANES

BACKGROUND OF THE INVENTION

The present invention relates to novel underarm formulations which contain volatile and/or non-volatile alkylmethylsiloxanes of the structure $(Me_2SiO)_a(MeRSiO)_b$ or $R'Me_2SiO(Me_2SiO)_y(MeRSiO)_zSiMe_2R''$, wherein a is 0-5, b is 1-6, a+b is 3-6, y is 0-100, z is 0-100, and R, R' and R'' are independently alkyls of 1-60 carbon atoms, with the proviso that at least one of R, R' or R'' is an alkyl of 4-60 carbon atoms. The present invention also relates to novel underarm formulations which contain non-volatile aralkylmethylsiloxanes of the structure $(Me_2SiO)_a(MeRSiO)_b$ or $R'Me_2SiO(Me_2SiO)_y(MeRSiO)_zSiMe_2R''$, wherein a is 0-5, b is 1-6, a+b is 3-6, y is 0-100, z is 0-100, y+z≧1, and R, R' and R'' are independently alkyls of 1-60 carbon atoms or aralkyls of 7-60 carbon atoms, with the proviso that at least one of R, R' or R'' is an aralkyl of 7-60 carbon atoms. Incorporation of these compounds unexpectedly provides novel properties to the formulation.

Many underarm compositions are known in the art and described in the cosmetic literature. Such compositions often contain polyorganosiloxanes because of the desirable characteristics they impart. These characteristics include, for example, volatility without cooling, lubricity, and non-tacky delivery of the active agents. The siloxanes incorporated into these compositions, however, are generally limited to those with short alkyl groups such as dimethylpolysiloxanes.

The incorporation of other volatile siloxanes into antiperspirant formulations is also known in the art. For instance Bolich in U.S. Pat. No. 5,002,762 describes antiperspirant compositions incorporating siloxanes of the structure:

$R_3SiO[R_2SiO]_xSiR_3$ wherein x=1 to 4, the total carbons ≦14, R is independently C1-C10 alkyl or trialkyl siloxy, and at least one R per molecule must be selected from aryl, alkylaryl, aryl alkyl, C1-C7 hydroxyalkyl, or R1-R2 wherein R1=C1-C9 alkylene and R2 is selected from a wide variety of substituents such as esters, amides, acids, cyanos, etc. Since these materials have a limited number of carbon atoms and contain the above R groups, they do not encompass the materials claimed in the present invention.

Various utilities for alkylmethylsiloxane polymers and copolymers are also known in the art. For instance, Th. Goldschmidt AG product literature on "ABIL® Silicones" reports that certain polysiloxane polyalkylene copolymers known as ABIL®-WAX 9800 and ABIL®-WAX 9801 have utility in skin care applications such as day creams, all purpose creams and body lotions. This literature, however, does not suggest the use of these agents in underarm formulations.

Similarly. U.S. Pat. No. 4,574,082 issued Mar. 4, 1986 describes cosmetics containing a dimethylpolysiloxane in admixture with an organopolysiloxane such as polymethyloctylsiloxane and polymethyloctadecylsiloxane. It is described therein that such mixtures inhibit the phase separation which occurs when waxes are mixed with dimethylsiloxanes. Again, however, this reference does not describe the use of these agents in underarm formulations.

What was not described in the prior art, therefore, is the incorporation of the presently claimed alkylmethylsiloxanes into underarm formulations. The present inventors have now discovered that underarm formulations containing such agents have many desirable characteristics such as modified hardness, reduced whitening, improved feel, compatibilization of ingredients, and controlled vapor pressure.

SUMMARY OF THE INVENTION

The present invention is directed to underarm formulations which contain volatile and/or non volatile alkylmethylsiloxanes of the structure $(Me_2SiO)_a(MeRSiO)_b$ or $R'Me_2SiO(Me_2SiO)_y(MeRSiO)_zSiMe_2R''$, wherein a is 0-5, b is 1-6, a+b is 3-6, y is 0-100, z is 0-100, and R, R' and R'' are independently alkyls of 1-60 carbon atoms, with the proviso that at least one of R, R' or R'' is an alkyl of 4-60 carbon atoms. The present invention also relates to novel underarm formulations which contain non-volatile aralkylmethylsiloxanes of the structure $(Me_2SiO)_a(MeRSiO)_b$ or $R'Me_2SiO(Me_2SiO)_y(MeRSiO)_zSiMe_2R''$, wherein a is 0-5, b is 1-6, a+b is 3-6, y is 0-100, z is 0-100, y+z≧1, and R, R' and R'' are independently alkyls of 1-60 carbon atoms or aralkyls of 7-60 carbon atoms, with the proviso that at least one of R, R' or R'' is an aralkyl of 7-60 carbon atoms. These formulations may contain other components such as astringent antiperspirant compounds, antimicrobial actives, adsorbents, absorbents, conventional volatile silicones, suspending agents, conventional waxes, emollients, perfumes, coloring agents, and other ingredients normally used in making underarm products.

These and other features, objects and advantages of the present invention will be apparent upon consideration of the following detailed description of the invention.

DETAILED DESCRIPTION OF THE INVENTION

The present invention is based on the unexpected discovery that the incorporation of alkylmethylsiloxanes into underarm formulations adds novel properties thereto. Such novel underarm formulations can include, for example, antiperspirant and/or deodorant formulations and the like.

Conventional underarm products often contain numerous ingredients depending on factors such as the utility of the product, the final product form (i.e., solid, liquid, gel, etc.), the desired physical properties, etc. These ingredients include, for example, astringent antiperspirant compounds, antimicrobials, volatile silicones, suspending agents, waxes, adsorbents, emollients, perfumes, coloring agents, and the like. The novel formulations of the present invention have some or all of the above volatile silicones, emollients and/or waxes of the conventional formulations replaced with alkylmethylsiloxanes.

As set forth above, volatile silicones are often added to underarm formulations because of the beneficial properties they impart such as volatility without cooling, lubricity, and non-tacky delivery of the actives. The present inventors have now discovered that additional beneficial properties can be obtained by replacing some or all of these conventional volatile silicones with volatile alkylmethylsiloxanes. For instance, alkylmethylsiloxanes have lower vapor pressures than conventional dimethylsiloxanes. As such, the vapor pressure of a formulation can be tailored to regulate its drying time or to control its release of volatiles (for regulatory purposes). Volatile alkylmethylsiloxanes also vary the aesthetics of underarm formulations by providing a more lubricous feel than conventional formulations. Moreover, alkylmethylsiloxane increase the payout of underarm formulations such that tailored delivery of active agents can be achieved. Finally, since alkylmethylsiloxanes have a structure which contains both inorganic linkages and long carbon chains, they aid in compatibilizing the array of ingredients often contained in underarm formulations.

As noted above, conventional underarm formulations (especially sticks) also often contain waxy materials to provide a structure which can be sheared when applied to the skin. Conventional waxes have melting points in the range of about 30° to about 150° C. and can include materials such as beeswax, spermaceti, carnauba, bayberry, candelilla, montan, ozokerite, ceresin, paraffin, microcrystalline wax, fatty acids with 8-20 carbon atoms, fatty alcohols containing from about 8 to about 30 carbon atoms, and fatty acid ester such as hydrogenated castor oil. Such waxes, however, often suffer from various disadvantages such as variability in hardness, a crystalline structure which causes them to crumble upon application, difficulties in obtaining and processing the materials, and the like. By replacing some or all of these waxes with alkylmethylsiloxanes, many of these disadvantages can be avoided. For instance, various physical properties of a formulation such as its melting point, hardness and texture can be tailored by altering the structure of the alkylmethylsiloxane. Likewise, the alkylmethylsiloxanes provide various processing advantages such as reproducible melt viscosity, better setting performance, and decreased surface tension because they can be produced in a purer form than the mixtures contained in naturally occurring waxes. In addition, since the alkylmethylsiloxanes are synthetic, they are generally more readily available than natural products. Finally, though the mechanism is unclear, incorporation of alkylmethylsiloxanes into underarm formulations also surprisingly reduces whitening of such formulations and, thus, provides improved aesthetics which are desired by consumers.

Additional non-volatile liquid siloxanes can also be incorporated into underarm formations. These can be used, for example, to replace or supplement conventional emollients and thereby provide formulations with a smoother feel.

Thus, underarm formulations with the above properties can be obtained by incorporating volatile and/or non-volatile alkylmethylsiloxanes of the structure

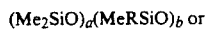
$(Me_2SiO)_a(MeRSiO)_b$ or

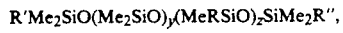
$R'Me_2SiO(Me_2SiO)_y(MeRSiO)_zSiMe_2R''$, wherein a is 0-5, b is 1-6, a+b is 3-6, y is 0-100, z is 0-100, R, R' and R'' are independently alkyls of 1-60 carbon atoms, with the proviso that at least 1 of R, R' and R'' is an alkyl of 4-60 carbon atoms, preferably 6-60 carbon atoms. Alternatively, the non-volatile aralkylmethylsiloxane can have the above structure wherein a is 0-5, b is 1-6, a+b is 3-6, y is 0 100, z is 0-100, y+z≧1,. and R, R' and R'' are independently alkyls of 1-60 carbon atoms or aralkyls of 7-60 carbon atoms, with the proviso that at least one of R, R' or R'' is an aralkyl of 7-60 carbon atoms. As is readily apparent to those skilled in the art, some of the above compounds are volatile and others are non-volatile liquids or waxes at room temperature. As such, one skilled in the art would know which materials may be used as volatile components and those which may be used as non-volatile components in underarm formulations. As used herein, the term "volatile" is used to describe those materials which have a vapor pressure of at least 0.01 mm Hg at 22° C.

Examples of non-volatile materials which are useful herein include liquids such as $[C_6H_{13}MeSiO]_4$, $Me_3SiO[Me_2SiO]_3[MeSiCH2CHMePhO]_6SiMe_3$, $Me_3SiO[Me_2SiO]_{95}[MeC_6H_{13}SiO]_5SiMe_3$, or $Me_3SiO[Me_2SiO]_{60}[MeC_6H_{13}SiO]_{40}SiMe_3$, and waxes such as $[C_{14}H_{29}MeSiO]_4$, $[C_{20}H_{41}MeSiO]_5$, $Me_3SiO[Me_2SiO]_3[MeC_{18}H_{37}SiO]_5SiMe_3$, $Me_3SiO[Me_2SiO]_3[MeC_{24}H_{49}SiO]_5SiMe_3$, $Me_3SiO[Me_2SiO]_{70}[MeC_{30}H_{61}SiO]_{30}SiMe_3$, $C_{18}H_{37}Me_2SiO(Me_2SiO)_{12}SiMe_2C_{18}H_{37}$, $C_{24}H_{49}Me_2SiO(Me_2SiO)_{12}SiMe_2C_{24}H_{49}$, and $Me_3SiO[MeC_{18}H_{37}SiO]_{10}SiMe_3$.

Examples of volatile materials include $Me_3SiOSiMe_2C_3H_7$, $Me_3SiOSiMe_2C_6H_{13}$, $[C_2H_5MeSiO]_4$, $[C_6H_{13}MeSiO]_4$, 8 $C_2H_5MeSiO]_5$, and $[C_2H_5MeSiO]_3$.

The above alkylmethylsiloxanes are known in the art and can be produced by known methods. For example, cyclic alkylmethylsiloxane polymers can be produced by the reaction of cyclic siloxanes having Si—H functional units thereon (e.g., $[MeHSiO]_a$) with a slight stoichiometric excess of an alkene in the presence of a platinum on carbon catalyst. Likewise, linear and cyclic alkylmethyl-dimethyl copolymers can be produced by the reaction of linear siloxanes having Si—H functionality in their chains (such as $(Me_3SiO_{0.5})_2(MeHSiO)_x$, in which x is about 4-100) with cyclic siloxanes having $(Me_2SiO)_x$ units, in which x is 3-6. The reaction product (generally about 10% cyclic and 90% linear) is then contacted with a slight stoichiometric excess of an alkene in the presence of a platinum on carbon catalyst.

Batch production of the alkylmethylsiloxanes is conducted by adding the reaction product to a non-agitated suspension of the catalyst in the alkene at about sixty degrees Celsius. Continuous production of the alkylmethylsiloxanes is conducted by pumping a preheated solution of a stoichiometric excess of an alkene CH₂=CHR and the siloxane having SiH functional units through a packed column containing platinum on carbon catalyst chips. The column will require provision for the removal of heat because of the exothermic nature of the reaction.

The materials are further processed in accordance with the present invention in order to provide a more cosmetically acceptable product by removing from the product any residual reactants and or by-products. The alkylmethyl polysiloxanes produced in accordance with the present invention have been found to contain at most about 0.5 percent residual alkene and about 99.5 percent alkylmethyl polysiloxane product. No measurable residual amount of platinum has been detected. The products are colorless, odorless, non-volatile, clear and stable materials.

In addition to the above alkylmethylsiloxanes, the underarm formulations of the present invention can also contain other conventional ingredients. These can include, for example, astringent antiperspirant compounds, antimicrobials adsorbents, absorbants, conventional volatile silicones, suspending agents, conventional waxes, emollients, perfumes, coloring agents, and the like.

Any conventional astringent antiperspirant compound can be used in accordance with the present invention. In general such materials comprise inorganic and organic salts of aluminum, zirconium, and zinc and mixtures thereof. Representative compounds are described throughout the patent literature in U.S. Pat. No. 4,280,994 issued Jul. 28, 1981: U.S. Pat. No. 4,369,173 issued Jan. 18, 1983; U.S. Pat. No. 4,425,328 issued Jan. 10 1984; U.S. Pat. No. 4,725,432 issued Feb. 16, 1988, and U.S. Pat. No. 4,822,603 issued Apr. 18 1989. Examples of such astringent antiperspirant compounds are aluminum chloride, aluminum chlorohydrate, aluminum dichlorohydrate, aluminum-zirconium chlorohydrate, aluminum chlorohydrex, aluminum-zirconium trichlorohydrate, aluminum-zirconium pentachlorohydrate, aluminum-zirconium tetrachlorohydrex glycine, aluminum-zirconium octachlorohydrate, aluminum sesquichlorohydrate, aluminum sulfate, zinc sulfate, zirconium chlorohydrate, aluminum-zirconium chlorohydroglycine, zirconium hydroxychloride, sodium aluminum lactate, sodium aluminum chlorohydroxy lactate, zinc sulfocarbolate, aluminum bromide, zinc phenolsulfonate aluminum sulfate and aluminum bromohydrate. In addition, it is contemplated that the above antiperspirants may be coated by techniques known in the art such as that described in U.S. Pat. No. 4,524,062, granted Jun. 18. 1985.

Conventional volatile silicones may also be used in the present invention. Generally such silicones comprise cyclic and linear polyalkyl siloxanes of the structures $[Me_2SiO]_x$ and $(Me_3SiO)_2[Me_2SiO]_y$ respectively, wherein x is 3 to 7, y is 1 to 5, and Me is methyl. Such materials generally have viscosities less than about 10 centistokes and have a measurable vapor pressure.

Conventional waxy materials which may be employed in accordance with the present invention include high and low melting point waxes, gums, resins, polymers, starches and elastomers. Exemplary high melting point waxes are insect and animal waxes such as beeswax and spermaceti; vegetable waxes such as candelilla, carnauba, Japan wax, Ouricury, Douglas-fir bark wax, rice-bran wax, jojoba wax, castor wax and bayberry wax; mineral waxes such as montan wax, peat wax, ozokerite and ceresin; petroleum waxes such as paraffin wax; synthetic waxes such as polyethylene waxes, Fischer-Tropsch waxes, chemically modified hydrocarbon waxes and substituted amide waxes; and conventional silicone wax. A particularly preferred high melting point wax is hydrogenated castor oil. Reference may be had to U.S. Pat. No. 3,395,941 issued Jul. 30, 1968 describing a silicone wax which is an organosilicon block copolymer; and U.S. Pat. No. 3,563,941 issued Feb. 16, 1971 describing a silicone-carnauba wax copolymer. Examples of low melting point waxes include fatty acids, fatty alcohols, fatty acid esters, and fatty acid amides having carbon chains of 3 to 30 carbon atoms. Particularly preferred low melting point waxes include stearyl alcohol, cetyl alcohol, myristyl alcohol and palmitic acid. U.S. Pat. No. 4,822,603, issued Apr. 18, 1989 describes many of these materials in detail.

The present invention may also contain fillers, suspending agents and other particulate material. These include, for example, talc, colloidal silica, clays and the like. Such materials are well known in the art and described in the literature.

Emollients, perfumes, colorants, emulsifiers and other ingredients normally used in making underarm products may also be used herein. Such materials are well known in the art and are described throughout the patent literature such as in U.S. Pat. Nos. 4,280,994: 4,425,328: 4,725,432; and 4,822,603.

The above ingredients are processed by conventional techniques to form the desired product. Using such techniques, gels, roll-ons, aerosols, pump sprays, and solid sticks may all be formed herein. If a solid stick is desired, is can be formed, for instance, by heating any wax materials while gently stirring. When the wax or waxes are melted and mixed thoroughly, any additional ingredients are added. The melt is then poured into a desired mold and allowed to cool to its solidification point. Alternatively, the above melt may be cooled and the additional ingredients added at a temperature just above the solidification point followed by pouring the mixture into a mold. In still another method, all of the ingredients are combined and heated above the melting point of the waxes. The composition is then cooled and poured into molds. If a liquid is desired (e.g., for roll-ons and sprays), it can be obtained by simply dissolving or dispersing the solids in solvents or liquids (e.g., alcohols).

The ingredients and amounts thereof to be included in the present invention are selected to produce the desired formulation. Generally, if a wax is to be included (e.g., for a stick), it is generally present in an amount of from about 0.5 to about 50% by weight. Active antiperspirant compounds are generally present in formulations in an amount of between about 3 and about 70% by weight. The total volatile silicone content of such formulations is generally in the range of between about 5 and about 80% by weight. Additional ingredients are added make up the remainder of the desired product form.

The formulations of the present invention are used in the conventional manner by topically applying an effective amount of the composition to areas of the body prone to perspiration.

The following examples are set forth in order to illustrate formulations prepared in accordance with the present invention.

EXAMPLE 1

In this Example, 8 antiperspirant sticks were produced having the following generic formulation:

| | | |
|---|---|---|
| 1) $[Me_2SiO]_5$-$Me_2SiO]_6$ mixture | 42% |
| 2) Alkylmethylsiloxane | 10% |
| 3) Stearyl Alcohol | 20% |
| 4) Hydrogenated Castor Oil | 4% |
| 5) PEG-8 Distearate | 2% |
| 6) Aluminum Zirconium Tetrachlorohydrex-Gly | 20% |

In addition, a control stick was made containing no alkylmethylsiloxane and 52% of ingredient #1.

The above sticks were made by charging a container equipped for reflux with ingredients 1-5. This mixture was heated to 75° C. and stirred until all of the solids had dissolved. Ingredient 6 was added to the mixture and uniformly dispersed by stirring. The mixture was then slowly cooled to about 46° C. and cast into the stick containers.

The following table lists several characteristics of the sticks. The alkylmethylsiloxanes used therein were as follows: 1=Me$_3$SiO[Me$_2$SiO]$_{95}$[MeC$_6$H$_{13}$SiO]$_5$SiMe$_3$, 2=Me$_3$SiO[Me$_2$SiO]$_7$[MeC$_6$H$_{13}$SiO]$_1$SiMe$_3$, 3=Me$_3$SiO[Me$_2$SiO]$_{60}$[MeC$_6$H$_{13}$SiO]$_{40}$SiMe$_3$, 4=C$_{18}$H$_{37}$Me$_2$SiO(Me$_2$SiO)$_{12}$SiMe$_2$C$_{18}$H$_{37}$, 5=C$_{24}$H$_{49}$Me$_2$SiO(Me$_2$SiO)$_{12}$SiMe$_2$C$_{24}$H$_{49}$, 6=C$_{30}$H$_{61}$Me$_2$SiO(Me$_2$SiO)$_{12}$SiMe$_2$C$_{30}$H$_{61}$, 7=Me$_3$SiO[Me$_2$SiO]$_{60}$[MeC$_{18}$H$_{37}$SiO]$_{40}$SiMe$_3$, and 8=Me$_3$SiO[MeC$_{18}$H$_{37}$SiO]$_{10}$SiMe$_3$.

TABLE 1

| Ex No | Form (1) | Mw | Compatible (2) | Cavitation (3) | Penetration (4) | White (5) |
|---|---|---|---|---|---|---|
| C$^6$ | — | — | Y | M | M | 4 |
| 1 | L | 7912 | N | L | H | 4 |
| 2 | L | 824 | N | L | M | 3 |
| 3 | L | 10362 | N | L | L | 3 |
| 4 | L | 1526 | Y | H | M | 2 |
| 5 | S | 1694 | Y | M | M | 1 |
| 6 | S | 1862 | Y | M | M | 1 |
| 7 | S | 17082 | Y | L | M | 1 |
| 8 | S | 3282 | Y | L | L | 1 |

(1) Form of the alkylmethylsiloxane - L = liquid, S = solid
(2) Compatibility of melt - N = no, Y = yes
(3) Cavitation or shrinkage of the stick on cooling - H = statistically higher than the control stick, M = statistically the same as the control stick and L = statistically lower than the control stick
(4) Penetration = hardness of the stick - H, M, and L have the same definition as in #3
(5) White = amount of whitening from the stick when applied to a black ceramic tile - 1 = least white - 4 = most white
(6) Control stick

EXAMPLE 2

In this Example, antiperspirant sticks having the following formulations were produced:

|  | Control | A | B |
|---|---|---|---|
| 1) Me$_3$SiOSiMeC$_6$H$_{13}$OSiMe$_3$ | — | 52% | 26% |
| 2) [Me$_2$SiO]$_5$-Me$_2$SiO]$_6$ mixture | 52% | — | 26% |
| 3) Stearyl Alcohol | 20% | 20% | 20% |
| 4) Hydrogenated Castor Oil | 4% | 4% | 4% |
| 5) PEG-8 Distearate | 4% | 4% | 4% |
| 6) Aluminum Zirconium Tetrachlorohydrex-Gly | 20% | 20% | 20% |

The above sticks were made by charging a container equipped for reflux with ingredients 1-5. This mixture was heated to 70° C. and stirred until all of the solids have dissolved. Ingredient 6 was added to the mixture and uniformly dispersed by stirring. The mixture was then slowly cooled to about 45° C. and cast into the stick containers.

The sticks of the present invention had a more lubricous feel than that of the control and they maintained this feel for a longer period of time.

EXAMPLE 3

In this Example, 4 antiperspirant roll-ons were produced having the following formulations:

|  | Control | A | B | C |
|---|---|---|---|---|
| 1) [Me$_2$SiO]$_5$-Me$_2$SiO]$_6$ mixture | 70% | — | 35% | 70% |
| 2) Volatile Alkylmethylsiloxane(1) | — | 70% | 35% | — |
| 3) Non-volatile Alkylmethylsiloxane(2) | — | — | — | 5% |
| 4) Dimethylpolysiloxane fluid, 50 cst | 5% | 5% | 5% | 5% |
| 5) Bentone V55 gel ® (Rheox Co.) | 3% | 3% | 3% | 3% |
| 6) Ethanol 95 | 2% | 2% | 2% | 2% |
| 7) Aluminum Zirconium Tetrachlorohydrex-Gly | 20% | 20% | 20% | 20% |

The above roll-ons were made by charging a container equipped for reflux with ingredients 1, 2, 5 and 6 followed by mixing to swell/disperse the clay. Ingredients 3, 4, and 7 were then added and uniformly dispersed. The mixture was then poured into appropriate roll-on containers.

The roll-ons of the invention had less whitening than the control.

EXAMPLE 4

In this Example, 2 antiperspirant pump sprays were produced having the following formulations:

|  | A | B |
|---|---|---|
| 1) Aluminum chloride hydroxide | 23.4% | 23.4% |
| 2) Ethanol 95% | 54.6% | 54.6% |
| 3) Propylene Glycol 3 Myristyl Ether | 10.0% | 10.0% |
| 4) Stearic Acid | 2.0% | 2.0% |
| 5) [SiMe$_2$O]$_5$ | 10.0% | — |
| 6) Volatile Alkylmethylsiloxane Fluid | — | 10.0% |

The ingredients were added to a container in the order listed —each ingredient being dissolved before adding the next. Both resultant formulations were clean. Formulation B was less cooling upon drying and less whitening on the skin.

EXAMPLE 5

In this Example, 4 antiperspirant sticks were produced having the following formulations:

|  | Control | A | B | C |
|---|---|---|---|---|
| 1) [Me$_2$SiO]$_5$-Me$_2$SiO]$_6$ mixture | 55% | 55% | 55% | 55% |
| 2) Stearyl Alcohol | 20% | 20% | 20% | 20% |
| 3) Castor Wax MP80 | 1% | — | — | — |
| 4) Alkylmethylsiloxane wax | — | 1% | 1% | 1% |
| 5) PPG-14 Butyl Ether | 2% | 2% | 2% | 2% |
| 6) Talc | 2% | 2% | 2% | 2% |
| 7) Aluminum Zirconium Tetrachlorohydrex-Gly | 20% | 20% | 20% | 20% |

The alkylmethylsiloxane waxes were as follows: A=Me$_3$SiO[MeC$_{30}$H$_{61}$SiO]SiMe$_3$, B=C$_{30}$H$_{61}$Me$_2$SiO[Me$_2$SiO]$_{12}$SiMe$_2$C$_{30}$H$_{61}$ and C=[MeSiC$_{30}$H$_{61}$O]$_4$ The above sticks were made by charging a container equipped for reflux with ingredients 1-6. This mixture was heated to 75° C. and stirred until all of the solids had dissolved. Ingredient 7 was added to the mixture and uniformly dispersed by stirring. The mixture was then slowly cooled to about 46° C. and cast into the stick containers.

The sticks of the present invention (A, B, and C) had a more lubricous feel and the perception lasted longer than that of the control. In addition, the sticks of the present invention were softer and had reduced whitening when compared with the control.

That which is claimed is:

1. In an antiperspirant, deodorant or antiperspirant and deodorant underarm formulation in a form selected from the group consisting of sticks, gels, roll-ons, pump sprays and aerosols which contains at least one material selected from the group consisting of astringent antiperspirant compounds, antimicrobials, adsorbents, absorbents, masking agents, and perfumes, the improvement comprising the incorporation of an effective amount of a nonvolatile alkylmethylsiloxane having a structure selected from the group consisting of $(Me_2SiO)_a(MeRSiO)_b$ and $R'Me_2SiO(Me_2SiO)_y(MeRSiO)_zSiMe_2R''$, wherein a is 0-5, b is 1-6, a +b is 3-6, y is 0-100, z is 0-100, and R, R' and R'' are independently alkyls of 1-60 carbons atoms, with the proviso that at least 1 of R, R' and R41 is an alkyl of 4-60 carbon atoms.

2. The formulation of claim 1 wherein said formulation also contains at least one material selected from the group consisting of volatile silicones, suspending agents, waxy material, emollients, and coloring agents.

3. The formulation of claim 1 wherein the alkylmethylsiloxane is present in an amount of from about 0.5 to about 50% by weight.

4. The formulation of claim 2 wherein an alkylmethylsiloxane is present in an amount of from about 0.5 to about 80% by weight, an active antiperspirant compound is present in an amount of between about 3 and about 70% by weight, and a volatile silicone is present in an amount of between about 5 and about 80% by weight.

5. In an antiperspirant, deodorant or antiperspirant and deodorant underarm formulation in a form selected from the group consisting of sticks, gels, roll-ons, pump sprays and aerosols which contains at least one material selected from the group consisting of astringent antiperspirant compounds, antimicrobials, adsorbents, absorbents, masking agents, and perfumes, the improvement comprising the incorporation of an effective amount of a nonvolatile aralkylmethylsiloxane having a structure selected from the group consisting of $(Me_2SiO)_a(MeRSiO)_b$ and $R'Me_2SiO(Me_2SiO)_y(MeRSiO)_zSiMe_2R''$, wherein a is 0-5, b is 1-6, a +b is 3-6, y is 0-100, z is 0-100, y+z≧1, and R, R' and R'' are independently alkyls of 1-60 carbon atoms or aralkyls of 7-60 carbon atoms, with the proviso that at least 1 of R, R' and R'' is an aralkyl of 7-60 carbon atoms.

6. The formulation of claim 5 wherein said formulation also contains at least one material selected from the group consisting of volatile silicones, suspending agents, waxy material, emollients, and coloring agents.

7. The formulation of claim 5 wherein the alkylmethylsiloxane is present in an amount of from about 0.5 to about 50% by weight.

8. The formulation of claim 6 wherein an alkylmethylsiloxane is present in an amount of from about 0.5 to about 80% by weight, an active antiperspirant compound is present in an amount of between about 3 and about 70% by weight, and a volatile silicone is present in an amount of between about 5 and about 80% by weight.

9. In an antiperspirant, deodorant or antiperspirant and deodorant underarm formulation in a form selected from the group consisting of sticks, gels, roll-ons, pump sprays and aerosols which contains at least one material selected from the group consisting of astringent antiperspirant compounds, antimicrobials, adsorbents, absorbents, masking agents, and perfumes, the improvement comprising the incorporation of volatile alkylmethylsiloxanes of the structure $[Me_2SiO]a[MeRSiO]_b$ or $R'Me_2SiO(Me_2SiO)_x(MeRSiO)_ySiR''Me_2$, wherein a is an integer of 0-5, b is an integer of 1-6, a+b=3-6, x is an integer of 0 to 6 inclusive, y is an integer of 0 to 6 inclusive, and R, R' and R'' are independently alkyls of 1-60 carbon atoms, with the proviso that at least one of R, R' and R'' is an alkyl of 4-60 carbon atoms.

10. The formulation of claim 9 wherein said formulation also contains at least one material selected from the group consisting of volatile silicones, suspending agents, waxy material, emollients, and coloring agents.

11. The formulation of claim 9 wherein the alkylmethylsiloxane is present in an amount of between about 0.5 and about 80% by weight.

12. The formulation of claim 10 wherein the total volatile siloxane is present in an amount of between about 0.5 and about 80% by weight, the wax is present in an amount of from about 0.5 to about 50% by weight, and the active antiperspirant compound is present in an amount of between about 3 and about 70% by weight.

13. In an antiperspirant, deodorant or antiperspirant and deodorant underarm formulations in a form selected from the group consisting of sticks, gels, roll-ons, pump sprays and aerosols which contains at least one material selected from the group consisting of astringent antiperspirant compounds, antimicrobials, adsorbents, absorbents, masking agents, and perfumes, the improvement comprising the incorporation of both a volatile and a non-volatile alkylmethylsiloxanes of the structure $[Me_2SiO]a[MeRSiO]_b$ or $R'Me_2SiO(ME_2SiO)_x(MeRSiO)_ySiR''Me_2$, wherein a is an integer of 0-5, b is an integer of 1-6, a+b=3-6, x is an integer of 0 to 100 inclusive, y is an integer of 0 to 100 inclusive, and R, R' and R'' are independently alkyls of 1-60 carbon atoms, with the proviso that at least one of R, R' and R'' is an alkyl of 4-60 carbon atoms.

14. The formulation of claim 13 wherein said formulation also contains at least one material selected from the group consisting of volatile silicones, suspending agents, waxy material, emollients, and coloring agents.

15. The formulation of claim 14 wherein the total volatile siloxane is present in an amount of between about 0.5 and about 80% by weight, the wax is present in an amount of from about 0.5 to about 50% by weight, and the active antiperspirant compound is present in an amount of between about 3 and about 70% by weight.

* * * * *